US012599596B2

(12) United States Patent
Zhang et al.

(10) Patent No.: US 12,599,596 B2
(45) Date of Patent: Apr. 14, 2026

(54) ANTI-TUMOR PHARMACEUTICAL COMPOSITION BASED ON IMMUNE CHECKPOINT BLOCKADE AND USE THEREOF

(71) Applicant: Shanghai Hui Tian Jin Ze Biotech Co., Ltd., Shanghai (CN)

(72) Inventors: Biao Zhang, Shanghai (CN); Sanhong Liu, Shanghai (CN)

(73) Assignee: Shanghai Hui Tian Jin Ze Biotech Co., Ltd., Shanghai (CN)

( * ) Notice: Subject to any disclaimer, the term of this patent is extended or adjusted under 35 U.S.C. 154(b) by 0 days.

(21) Appl. No.: 18/955,328

(22) Filed: Nov. 21, 2024

(65) Prior Publication Data

US 2025/0127769 A1      Apr. 24, 2025

Related U.S. Application Data

(63) Continuation of application No. PCT/CN2024/100159, filed on Jun. 19, 2024.

(30) Foreign Application Priority Data

Aug. 30, 2023      (CN) ......................... 202311099032.7

(51) Int. Cl.
| | |
|---|---|
| *A61K 31/4525* | (2006.01) |
| *A61K 31/00* | (2006.01) |
| *A61K 31/355* | (2006.01) |
| *A61K 38/22* | (2006.01) |
| *A61P 35/00* | (2006.01) |

(52) U.S. Cl.
CPC ........ *A61K 31/4525* (2013.01); *A61K 31/355* (2013.01); *A61K 31/658* (2023.05); *A61K 38/2292* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,632,825 B2 | 1/2014 | Velasco Diez | |
| 11,331,301 B2 | 5/2022 | Koltai | |
| 2003/0236236 A1 | 12/2003 | Chen et al. | |
| 2004/0029860 A1 | 2/2004 | Gil-Ad et al. | |

FOREIGN PATENT DOCUMENTS

| | | |
|---|---|---|
| CN | 102460165 A | 5/2012 |
| CN | 112386701 A | 2/2021 |
| CN | 116075296 A | 5/2023 |
| CN | 116253621 A | 6/2023 |
| CN | 116407525 A | 7/2023 |
| CN | 116568312 A | 8/2023 |
| CN | 116808176 A | 9/2023 |
| EP | 2080511 A2 | 7/2009 |
| RU | 2014144691 A | 5/2016 |
| WO | WO 2007/043057 A2 | 4/2007 |
| WO | 2016062289 A1 | 4/2016 |
| WO | WO 2022/026591 A1 | 2/2022 |

OTHER PUBLICATIONS

Abraham et al., Vitamin E and its anticancer effects. Critical Reviews in Food Science and Nutrition 59 (17):2831-2838, 2019.*
Costantini et al., A Reappraisal of Thymosin Alpha1 in Cancer Therapy. Front. Oncol., vol. 9, pp. 1-11, 2019.*
Jang et al., Anticancer activity of paroxetine in human colon cancer cells: Involvement of MET and ERBB3. J Cell Mol Med. Nov. 13, 2018;23(2):1106-1115.*
Chinese Search Report dated Oct. 8, 2023, issued in Chinese Patent Application No. 2023110990327, with English language translation.
PCT International Search Report dated Sep. 27, 2024, issued in PCT International Application No. PCT/CN2024/100159, with English language translation.
Zheng et al., "The Application of Antidepressant Drugs in Cancer Treatment," Biomedicine & Pharmacotherapy, vol. 157, No. 113985, 2023, available online Nov. 16, 2022, 11 pages.
Zhang et al., "The Regulatory Effect of Porcine Thymosin on Immune Function in Mice and Middle-Aged and Elderly Individuals," Journal of Shandong Medical University (Social Sciences Edition), vol. 28, Issue 3, Dec. 31, 1990, pp. 67-73, with English language Abstract.
Jan. 29, 2026 First Examination Report issued in connection with Australian Patent Application No. 2024314973.
Jan. 8, 2026 Office Action issued in connection with Japanese Patent Application No. 2025-509096.
Guedon, Marie, et al. "Cannabidiol-drug interaction in cancer patients: A retrospective study in a real-life setting." British Journal of Clinical Pharmacology 89.7 (2023): 2322-2328.

* cited by examiner

*Primary Examiner* — Ruixiang Li

(74) *Attorney, Agent, or Firm* — Amster, Rothstein & Ebenstein LLP

(57) ABSTRACT

Disclosed herein is an anti-tumor pharmaceutical composition based on immune checkpoint blockade and use thereof. The anti-tumor pharmaceutical composition comprises: paroxetine hydrochloride, and a T-cell enhancer, wherein the T-cell enhancer is at least one of vitamin E and thymosin. Through a series of in vitro and in vivo experiments, cannabidiol and paroxetine hydrochloride were first found to be capable of effectively reducing the expression of PD-L1 on the tumor cell membrane, thereby blocking the PD-1/PD-L1 signaling pathway and enhancing the ability of T cells to kill tumor cells. The T-cell enhancer added on this basis can further increase the quantity and activity of T cells, significantly increase the killing ability of T cells after immunosuppression is relieved, and greatly improve the anti-tumor effect of the drug. The components of the pharmaceutical composition used in the present invention, namely, cannabidiol, paroxetine hydrochloride, and vitamin E+thymosin, can exert a synergistic effect and improve the anti-tumor effect.

13 Claims, 11 Drawing Sheets

A
RKO
CBD (µM)    0    10    20    30    40
PD-L1
GAPDH

B
H1975
CBD (µM)    0    5    10    20
PD-L1
GAPDH

C
A549
CBD (µM)    0    0    5    10    20
IFN-γ       -    +    +    +    +
PD-L1
GAPDH

ANTI-TUMOR PHARMACEUTICAL COMPOSITION BASED ON IMMUNE CHECKPOINT BLOCKADE AND USE THEREOF

CROSS-REFERENCE TO RELATED APPLICATIONS

This application is a continuation of PCT International Patent Application No. PCT/CN2024/100159, filed Jun. 19, 2024, which claims benefit of Chinese Patent Application No. 202311099032.7, filed Aug. 30, 2023, the contents of each of which are hereby incorporated by reference.

TECHNICAL FIELD

The present invention relates to the field of medicine, specifically to an anti-tumor pharmaceutical composition based on immune checkpoint blockade and use thereof.

BACKGROUND

Since tumor immunology has been continuously innovated and developed, cancer immunotherapy (CIT) has achieved significant effects in various tumor therapies and has brought hope to patients with tumors.

Currently, in cancer immunotherapy, a relevant therapy against the immune checkpoints PD-1/PD-L1 has attracted much attention. Programmed cell death protein 1 (PD-1), an important immunosuppressive molecule, is widely expressed in activated T cells and is a surface receptor for activated T cells. A receptor of PD-1, programmed death ligand 1 (PD-L1), is hardly detectable in normal tissues but is highly expressed in many human tumor tissues. After PD-1 binds to PD-L1, an immunosuppressive signal is sent out to T cells, thereby inhibiting the activation of T cells, preventing T cells from killing tumor cells, and causing immune escape of tumors. Blocking the interaction of PD-1/PD-L1 can restore the functional effects of tumor-specific T cells. PD-1/PD-L1-related immune checkpoint inhibition therapy is an ideal means for cancer immunotherapy. Currently, various monoclonal antibodies aimed at PD-1/PD-L1 are on the market. Research has shown that the therapeutic effective rates of solid tumors with better responses to anti-PD-1/PD-L1 antibodies, such as melanoma, renal cancer, and non-small cell lung cancer, are positively correlated with positive PD-L1 expression. However, only a few patients benefit at present because of the many side effects of antibody therapy.

SUMMARY

The present invention provides a novel anti-tumor pharmaceutical composition based on immune checkpoint blockade and aims to address the problems of large side effects and small benefits for patients receiving existing anti-PD-1/PD-L1 antibody immunotherapy. The anti-tumor pharmaceutical composition can inhibit the expression of PD-L1 proteins on the surface of tumor cells, thereby blocking the PD-1/PD-L1 signaling pathway and enhancing the ability of T cells to kill tumor cells.

To solve this technical problem, the first objective of the present invention is to provide an anti-tumor pharmaceutical composition based on immune checkpoint blockade, comprising paroxetine hydrochloride and a T-cell enhancer, wherein the T-cell enhancer is at least one of vitamin E and thymosin.

Preferably, the anti-tumor pharmaceutical composition further comprises cannabidiol.

Preferably, the anti-tumor pharmaceutical composition comprises cannabidiol, paroxetine hydrochloride, vitamin E, and thymosin.

Preferably, in terms of pharmaceutical composition, cannabidiol, paroxetine hydrochloride, vitamin E, and thymosin have a dose mass ratio of (20-500):(1-100):(10-400):(1-60).

Preferably, the pharmaceutical composition further comprises at least one of a pharmaceutically acceptable carrier, an excipient, a wetting agent, an emulsifier and a pH buffer.

Preferably, the pharmaceutical composition has a dosage form of at least one of an oil, a granule, a tablet, a pulvis, a capsule, a microcapsule preparation, a pill, a powder, an oral liquid, a sol, a spray and an atomizing agent.

The second objective of the present invention is to provide an anti-tumor pharmaceutical composition based on immune checkpoint blockade. The anti-tumor pharmaceutical composition comprises: paroxetine hydrochloride and cannabidiol.

Another objective of the present invention is to provide use of the anti-tumor pharmaceutical composition based on immune checkpoint blockade in the preparation of an anti-tumor drug.

Preferably, the tumor comprises any one of the following: colorectal cancer, lung cancer, liver cancer, gastric cancer, bladder cancer, esophageal cancer, breast cancer, and melanoma.

Preferably, in terms of pharmaceutical composition, cannabidiol and paroxetine hydrochloride can inhibit the expression of PD-L1 proteins on the surface of tumor cells, thereby blocking the PD-l/PD-L1 signaling pathway and enhancing the ability of T cells to kill tumor cells.

Compared with the prior art, the present invention has at least the following beneficial effects:

(1) Through a series of in vitro cell experiments, cannabidiol (CBD) and paroxetine hydrochloride (PAR) were first found to be capable of effectively reducing the expression of PD-L1 on the surface of tumor cells, thereby blocking the PD-1/PD-L1 signaling pathway and enhancing the ability of T cells to kill tumor cells.

(2) The anti-tumor drug provided by the present invention is a combination of drugs based on immune checkpoint inhibition and the T cell enhancement, wherein cannabidiol and paroxetine hydrochloride can effectively inhibit the expression of PD-L1 on the surface of tumor cells and greatly relieve the inhibitory effect on the activation of T cells. In addition, on the basis, the added T-cell enhancer can further improve the quantity and activity of T cells and remarkably increase the killing capacity of T cells after immunosuppression is relieved, thereby significantly improving the antitumor effect of a drug through combined action. More importantly, compared with anti-PD-1/PD-L1 antibody immunotherapy, CBD and PAR, the drugs used in the present invention directly reduce the expression level of PD-L1 on the surface of tumor cells, are more effective and are less prone to cause damage of T cells to normal tissue and avoid side effects.

(3) An experiment revealed that the components of the pharmaceutical composition provided by the present invention, namely, cannabidiol, paroxetine hydrochloride, vitamin E, and thymosin, can exert synergistic effects and improve the anti-tumor effects.

A is a result of the expression of PD-L1 in RKO cells;

B is a result of PD-L1 expression in H1975 cells; and

C is a result of the expression of PD-L1 in A549 cells.

FIGS. 3A-3F are a comparison of the expression of PD-L1 on the cell membrane in different types of tumor cells treated with different concentrations of CBD.

A is a result of the expression of PD-L1 on the HCT116 cell membrane;

B is a result of the expression of PD-L1 on the RKO cell membrane;

C is a result of the expression of PD-L1 on the H460 cell membrane;

D is a result of the expression of PD-L1 on the A549 cell membrane;

E is a result of the expression of PD-L1 on the H1975 cell membrane; and

F is a result of the expression of PD-L1 on the HT29 cell membrane.

Figure 4:
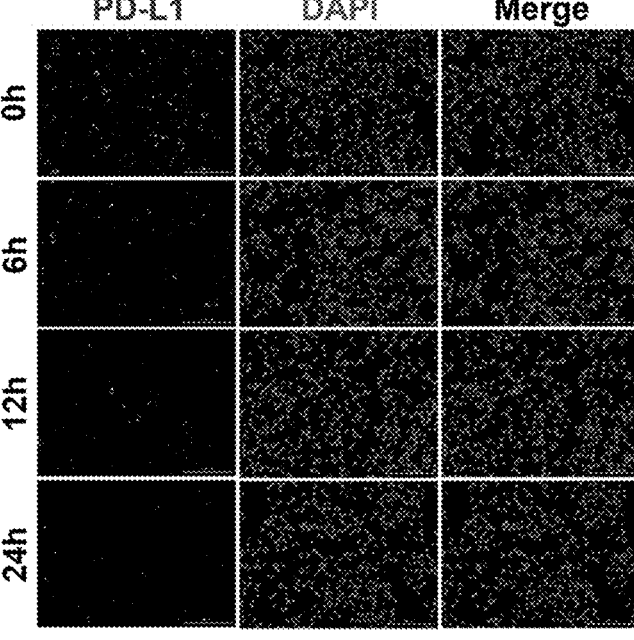

FIG. 4 is a comparison of the expression of PD-L1 on the cell membrane in RKO cells treated with the same concentration of CBD for different time.

Figure 5:
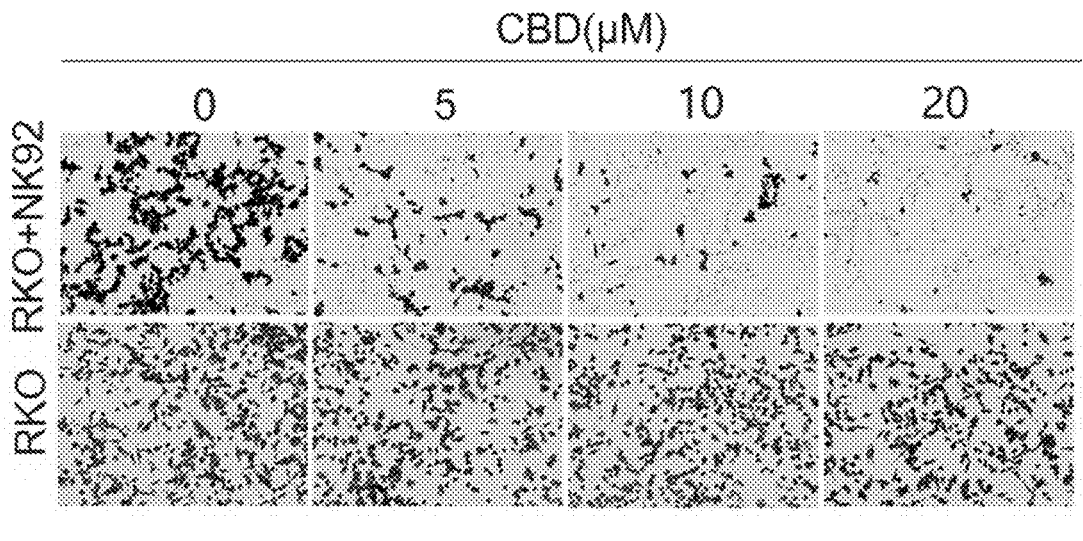
Figures 6A, 6B, 6C, 6D:
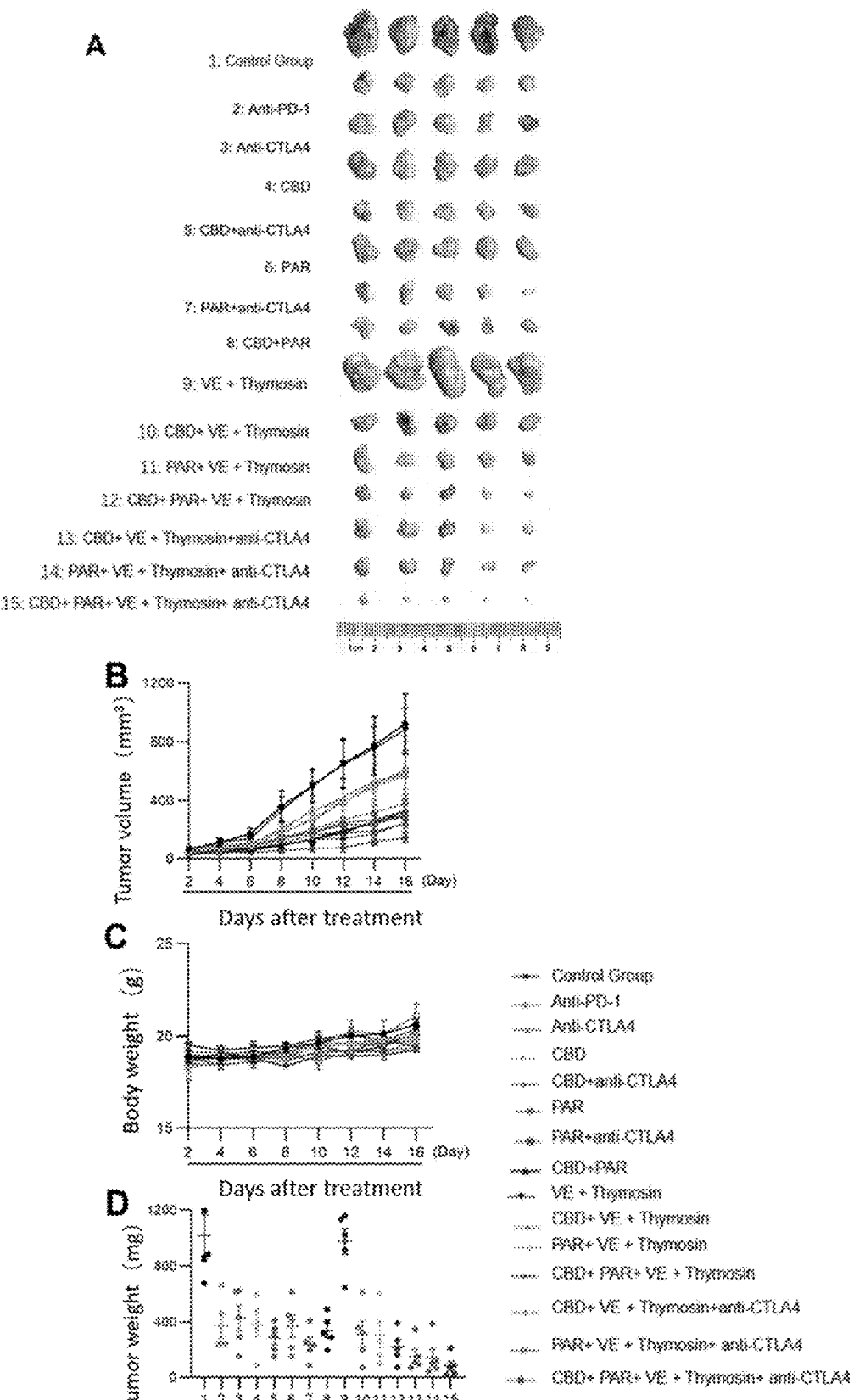
Figures 7A, 7B, 7C, 7D:
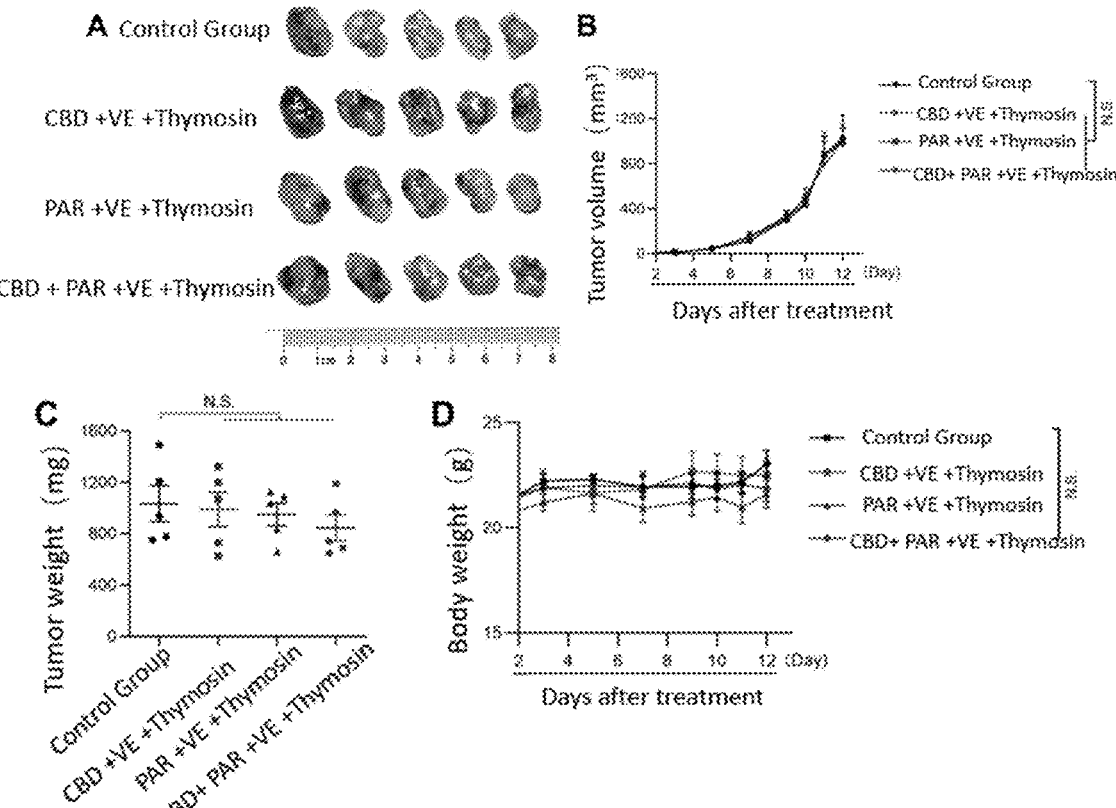
Figures 8A, 8B:
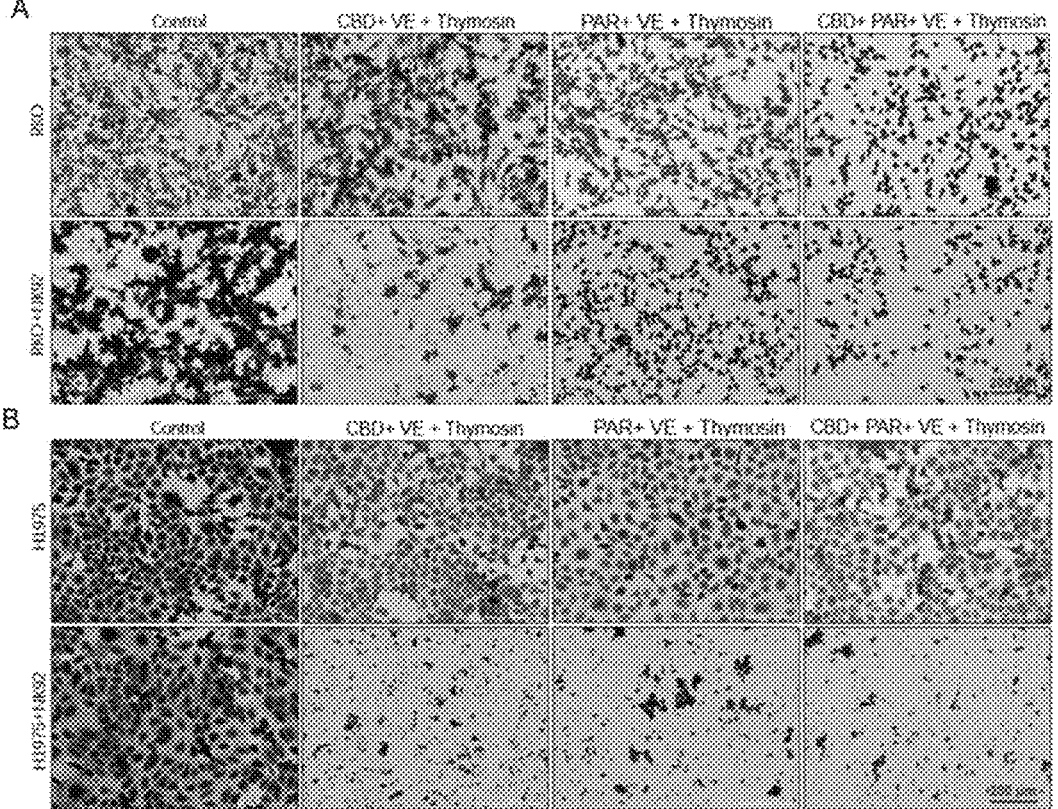
Figures 8C, 8D:
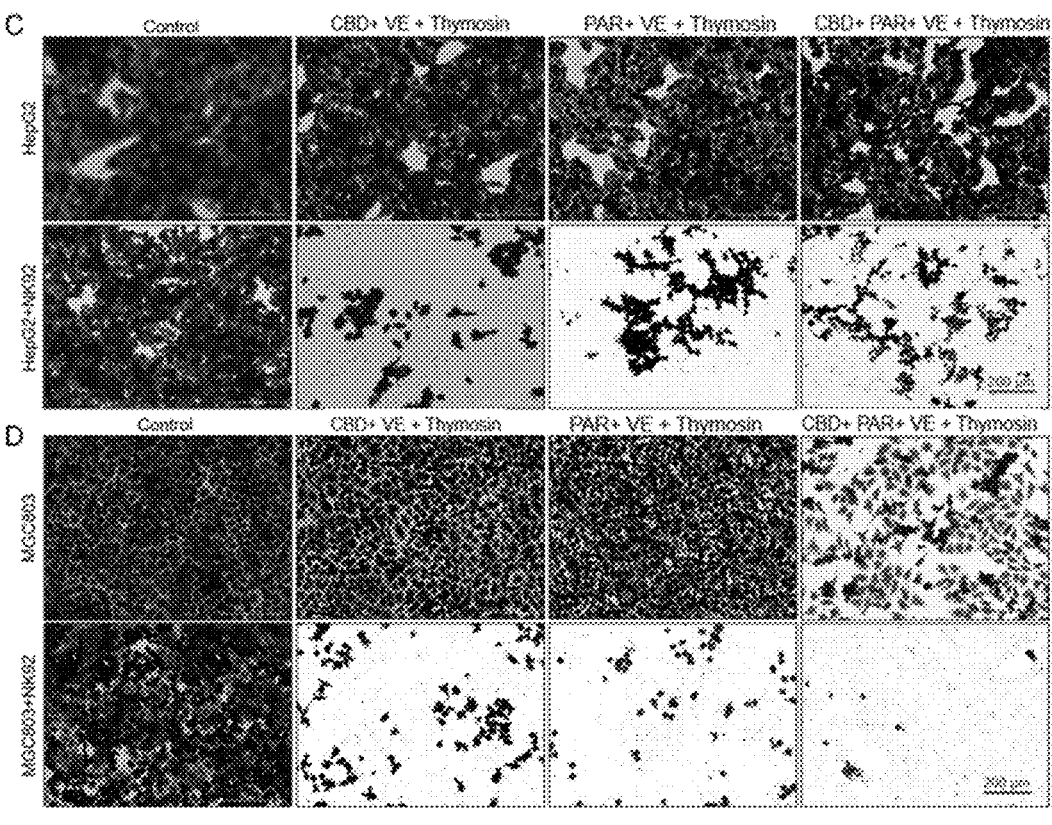

FIG. 5 is a comparison of the viability of RKO cells co-treated with CBD and NK92 cells.

FIGS. 6A-6D are a comparison of anti-tumor effects of mice with colorectal cancer treated with different pharmaceutical compositions, wherein, A shows tumor tissue photographs of each group of mice;

B shows growth curves of tumor volumes of each group of mice;

C shows growth curves of body weight of each group of mice; and

D shows growth curves of tumor weight of each group of mice.

FIGS. 7A-7D are a comparison of anti-tumor effects of colorectal cancer-immunodeficient mice treated with different pharmaceutical compositions, wherein, A shows tumor tissue photographs of each group of mice;

B shows growth curves of tumor volumes of each group of mice;

C shows growth curves of tumor weight of each group of mice; and

D shows growth curves of body weight of each group of mice.

FIGS. 8A-8D are a comparison of the viability of different types of tumor cells co-treated with 3 pharmaceutical compositions and NK92 cells, wherein, A is a comparison of the viability of RKO cells;

B is a comparison of the viability of H1975 cells;

C is a comparison of the viability of HepG2 cells; and

D is a comparison of the viability of MGC803 cells.

FIGS. 9E-9H are a comparison of the viability of different types of tumor cells co-treated with 3 pharmaceutical compositions and NK92 cells, wherein, E is a comparison of the viability of T24 cells;

F is a comparison of the viability of TE-5 cells;

G is a comparison of the viability of MCF-7 cells;

H is a comparison of the viability of B16-F10 cells; and wherein a control group refers to the group in which no drug is administrated.

Figures 9E, 9F:
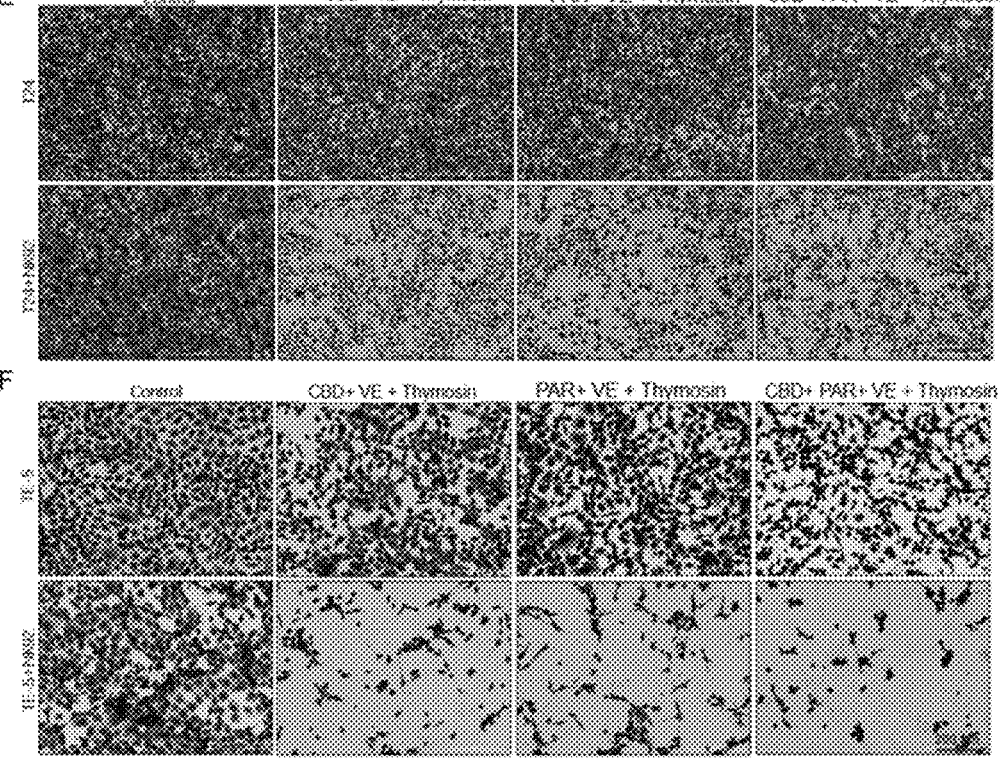
Figures 9G, 9H, 10:
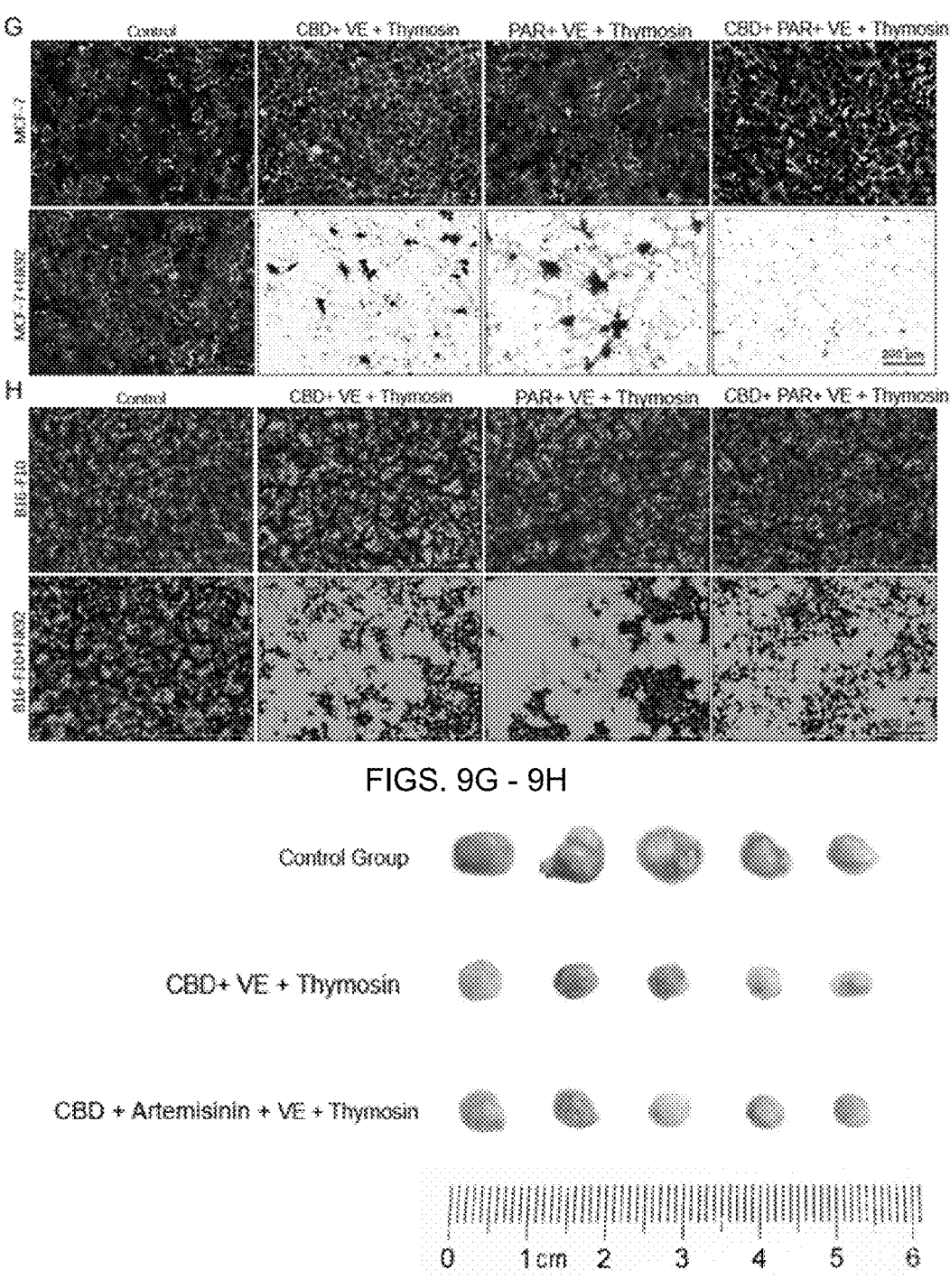

FIG. 10 is a comparison of the anti-tumor effects on mice with colorectal cancer treated with CBD+vitamin E+thymosin or CBD+artemisinin+vitamin E+thymosin.

Figure 11:
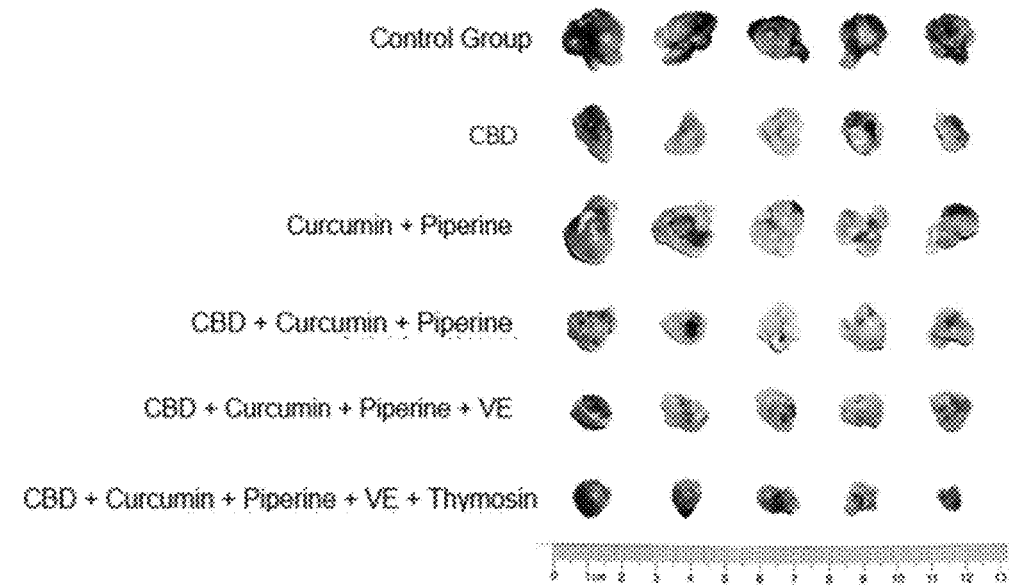
Figures 12A, 12B, 12C, 12D:
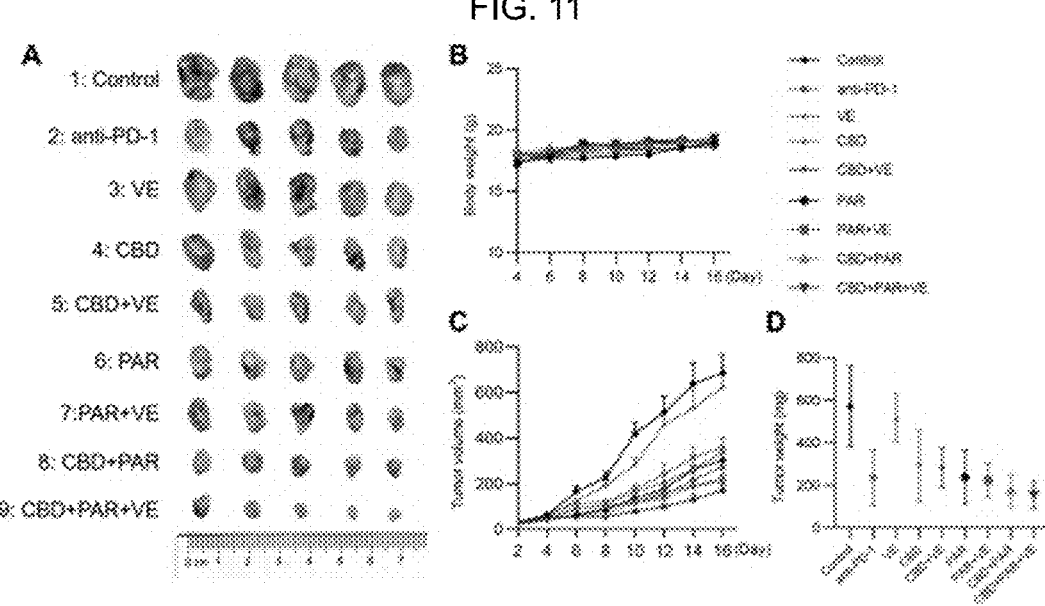
Figures 13A, 13B, 13C, 13D:
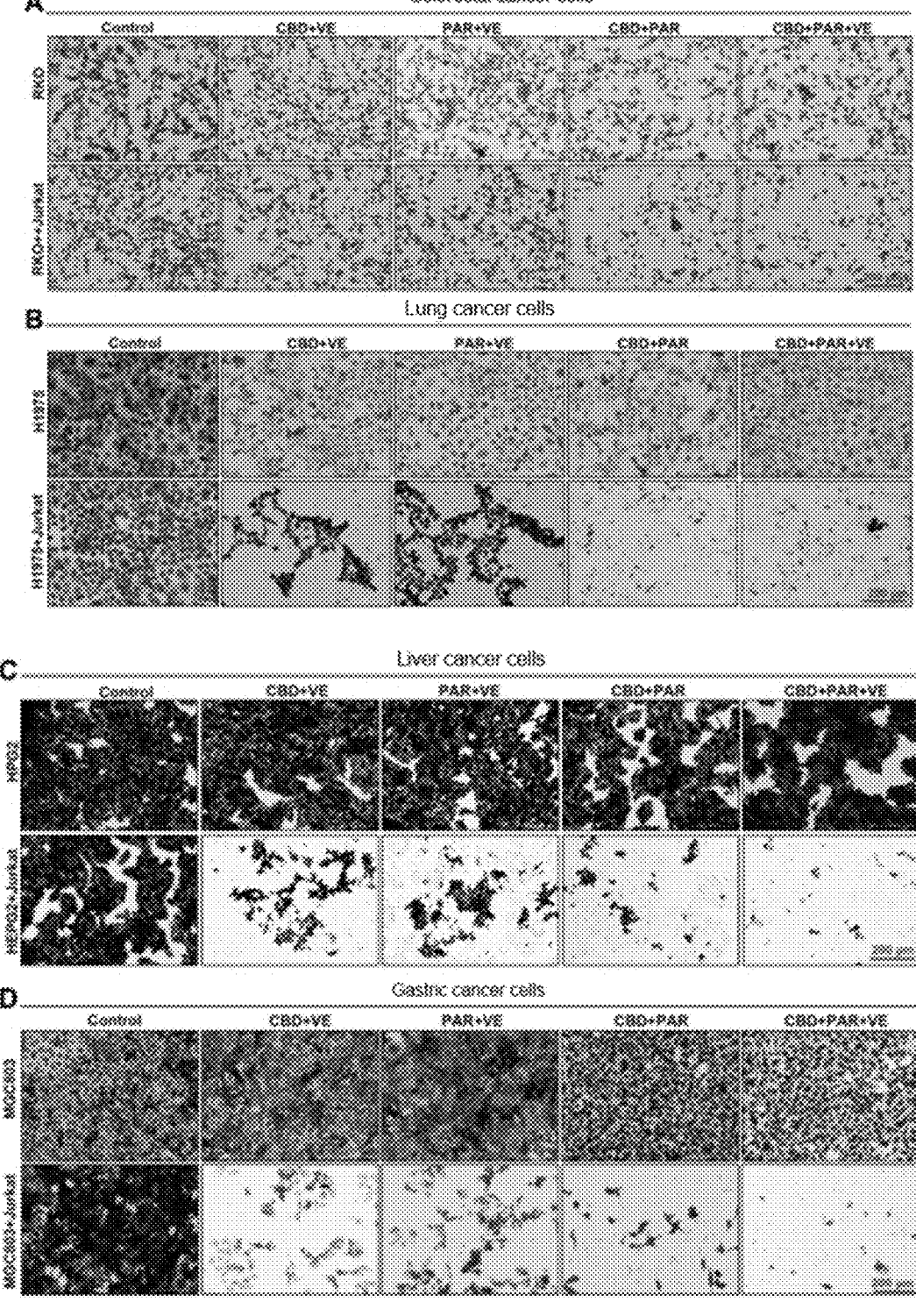
Figures 14A, 14B, 14C, 14D:
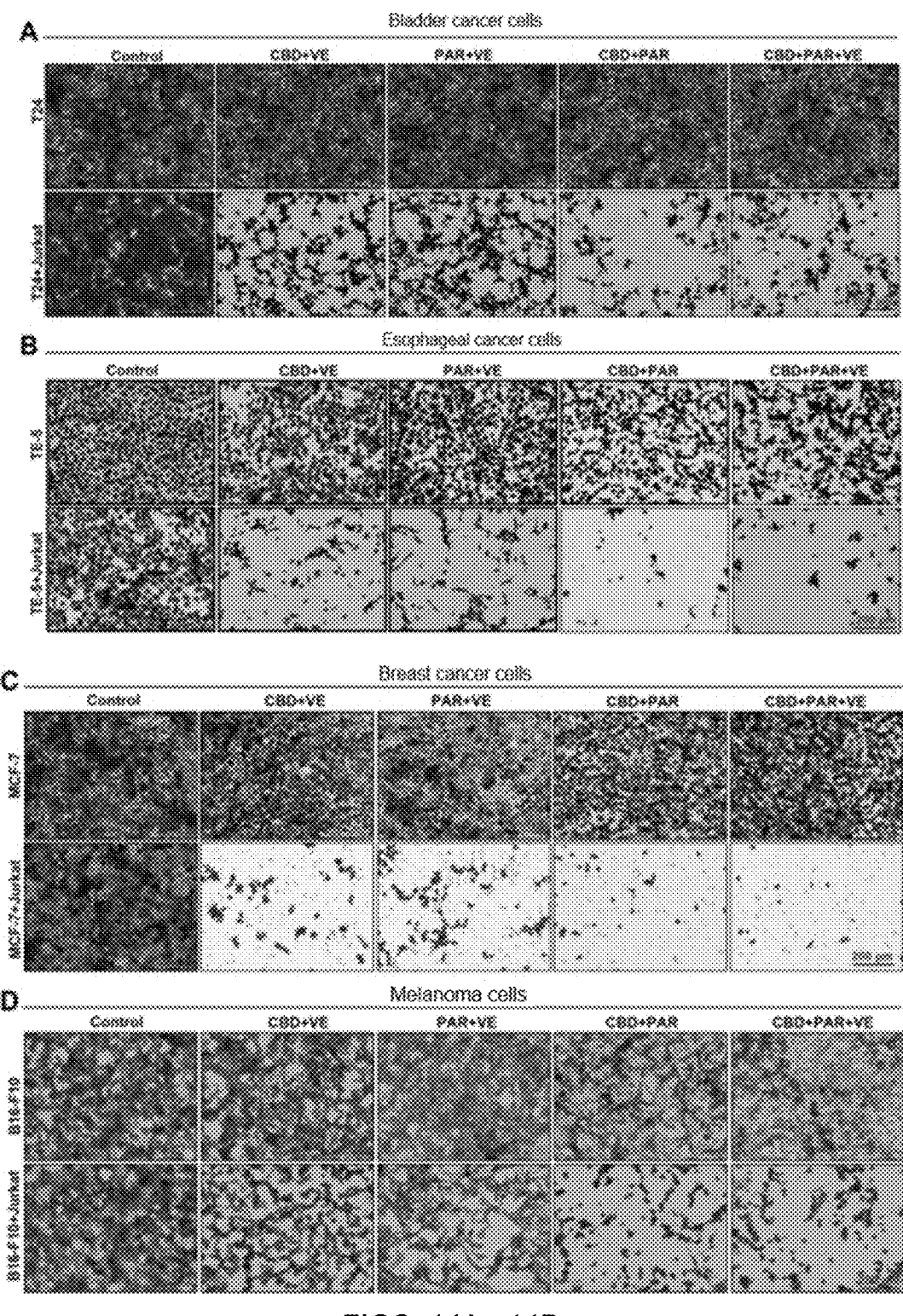

FIG. 11 is a comparison of anti-tumor effects on mice with colorectal cancer treated with CBD, curcumin+piperine, CBD+curcumin+piperine, CBD+curcumin+piperine+vitamin E, or CBD+curcumin+piperine+vitamin E+thymosin.

FIGS. 12A-12D are a comparison of anti-tumor effects of mice with colorectal cancer treated with different pharmaceutical compositions, wherein, A shows tumor tissue photographs of each group of mice;

B shows growth curves of body weight of each group of mice;

C shows growth curves of tumor volumes of each group of mice;

D shows the tumor weights of each group of mice.

FIGS. 13A-13D are a comparison of the viability of different types of tumor cells co-treated with 2 pharmaceutical compositions and Jurkat cells overexpressing PD-i, wherein, A shows a comparison of viability of RKO cells co-treated with CBD and PAR;

B shows a comparison of viability of H1975 cells co-treated with CBD and PAR;

C shows a comparison of viability of HepG2 cells co-treated with CBD and PAR;

D shows a comparison of viability of MGC803 cells co-treated with CBD and PAR.

FIGS. 14A-14D are a comparison of the viability of different types of tumor cells co-treated with 2 pharmaceutical compositions and Jurkat cells overexpressing PD-1, wherein, A shows a comparison of viability of T24 cells co-treated with CBD and PAR;

B shows a comparison of viability of TE-5 cells co-treated with CBD and PAR;

C shows a comparison of viability of MCF-7 cells co-treated with CBD and PAR;

D shows comparison of viability of B16-F10 cells co-treated with CBD and PAR.

DETAILED DESCRIPTION

As described in the background, existing anti-PD-1/PD-L1 antibody immunotherapy has several problems, such as severe side effects and limited benefits for patients. The expression of PD-L1 in tumor cells may affect the clinical efficacy of PD-1/PD-L1 related immune checkpoint therapy. A micromolecule that regulates the expression of PD-L1 in a targeted manner is expected to become a new therapeutic mode, and identifying a micromolecule that negatively regulates the expression of PD-L1 could become a new solution in the process of immunotherapy.

Therefore, the present invention aimed to identify a micromolecule that negatively regulates the expression of PD-L1 to block the PD-1/PD-L1 pathway in tumors, enhance the activity of T cells, and kill tumor cells. Through a large number of experimental screens and verifications, the present invention finally provides a novel anti-tumor pharmaceutical composition based on immune checkpoint blockade, comprising cannabidiol and/or paroxetine hydrochloride, and a T-cell enhancer. At the same time, the present invention also provides another novel anti-tumor pharmaceutical composition based on immune checkpoint blockade, comprising paroxetine hydrochloride and cannabidiol. Among them, Cannabidiol (CBD) is a *Cannabis sativa* extract that has been widely used in the fields of medical skin-care products, beverages and foods capable of improving mood. In recent years, although an increasing number of studies have shown that CBD has an anti-tumor activity in different types of tumors, the anti-tumor mechanism is not completely understood and greatly differs among different types of tumors. In addition, the present invention is the first to report that CBD can effectively reduce the expression of PD-L1 in tumors and is expected to be used in cancer immunotherapy.

Paroxetine hydrochloride (PAR) is an antidepressant. The present invention revealed that paroxetine hydrochloride also reduces the expression of PD-L1 in tumor cells, indicating that paroxetine hydrochloride can also be used as a candidate drug for negatively regulating the expression of PD-L1 in tumor cells.

On the basis of the above studies, the present invention further designs the combined use of CBD or PAR with a T-cell enhancer. The T-cell enhancers include any one or more of the following effects: (1) promoting the proliferation and differentiation of T cells and increasing the percentage or absolute quantity of T cells and (2) enhancing the activity of T cells and improving the immune functions of T cells. The design concept is as follows: CBD and PAR can reduce the expression of PD-L1 in tumor cells and greatly reduce the degree of inhibition of T cells activation. On this basis, the T-cell enhancer is added, the quantity and activity of T cells can be improved, and the ability of T cells to kill tumor cells is markedly increased after immunosuppression is relieved. If the T-cell enhancer is added when the expression of PD-L1 is not inhibited, even if the T-cell enhancer can promote the proliferation and differentiation of T cells, the activation of T cells can still be inhibited by the PD-1/PD-L1 pathway, and the effect of the T-cell enhancer is greatly reduced. Therefore, CBD or PAR can be combined with the T-cell enhancer for use because the pharmaceutical composition can exert a synergistic effect and improve the anti-tumor activity of the drug.

In some embodiments, the T-cell enhancer includes at least one of vitamin E and thymosin. Vitamin E is an important antioxidant and also an effective immunomodulator that can promote the development of immune organs in organisms and the differentiation of immune cells and improve the functions of cellular immunity and humoral immunity in these organisms. Thymosin is derived from a thymus tissue extract of a calf, a pig or a sheep and is a soluble polypeptide that can enhance the immune functions of T cells and can be used for treating congenital or acquired T cells immunodeficiency diseases, autoimmune diseases, and tumors.

In some embodiments, the anti-tumor pharmaceutical composition comprises cannabidiol, paroxetine hydrochloride, and vitamin E. Cannabidiol, paroxetine hydrochloride, and vitamin E have a dose ratio of (20-500):(1-100):(10-400).

In some embodiments, the anti-tumor pharmaceutical composition comprises cannabidiol, paroxetine hydrochloride, vitamin E, and thymosin. Cannabidiol, paroxetine hydrochloride, vitamin E, and thymosin have a dose ratio of (20-500):(1-100):(10-400):(1-60).

In some embodiments, the pharmaceutical composition further comprises a pharmaceutically acceptable carrier, an excipient, a wetting agent, an emulsifier and a pH buffer.

Suitable pharmaceutically acceptable carriers are well known to be skilled in the art. A sufficient description of pharmaceutically acceptable carriers can be found in Remington's Pharmaceutical Sciences. The pharmaceutically acceptable carriers in the compositions may comprise liquids such as water, phosphate buffered saline, ringer's solution, physiological saline, a balanced salt solution, glycerol or sorbitol, and the like. In addition, auxiliary substances such as a lubricant, a glidant, a wetting agent or an emulsifier, a pH buffering substance and a stabilizer, such as albumin and the like, may also be present in these carriers. In use, a safe and effective amount of the anti-tumor drug of the present invention is administered to a mammal (e.g., a human). The specific dose also takes into account factors such as the route of administration and the health of a patient, and the like, which are within the skill range of a skilled physician. The precise effective amount for a subject will depend upon the size and health of the subject, the nature and extent of the disorder, and the combination of a therapeutic agent and/or a therapeutic agent selected for administration. For a given condition, the effective amount can be determined via a routine experiment and can be determined by a clinician.

In some embodiments, the pharmaceutical composition has a dosage form of an oil, a granule, a tablet, a pulvis, a capsule, a pill, a powder, an oral liquid, a sol, a spray and an atomizing agent.

Another aspect of the present invention is the use of anti-tumor pharmaceutical composition based on immune checkpoint blockade in the preparation of an anti-tumor drug.

In some embodiments, the tumor comprises any one of the following: colorectal cancer, lung cancer, liver cancer, gastric cancer, bladder cancer, esophageal cancer, breast cancer, and melanoma.

The experimental process and experimental results of the present invention are described in detail below with reference to the accompanying drawings and embodiments so that the anti-tumor pharmaceutical composition of the present invention can inhibit the expression of PD-L1 proteins on the surface of tumor cells, thereby blocking the PD-1/PD-L1 signaling pathway and enhancing the ability of T cells to kill tumor cells.

Unless otherwise specified, the experimental methods used in the following embodiments are conducted conventionally or according to the conditions recommended by the manufacturers.

The materials, reagents, etc., used in the following embodiments are all commercially available unless otherwise specified. Among them, in Embodiments 1 to 4, cannabidiol was purchased from Yuxi Hongbao Biotechnology Co., Ltd.; paroxetine hydrochloride was purchased from MCE company with the article number BRL29060A; thymosin enteric-coated tablets were purchased from Heilongjiang Dilong Pharmaceutical Co., Ltd. (NMPA approval number H20058365); vitamin E (specifically in the form of a-tocopherol) was purchased from Shanghai Sunny Biotech Co., Ltd. (article number A04GS156945); anti-PD-1 was purchased from Bioxcell company (Ultra-LEAF™ purified anti-mouse CD279 (PD-1, BE0146)); corn oil was purchased from GOLD SUN Grain and Oil Co., Ltd.; curcumin was purchased from the MCE company with the article number HY-N0005; capsaicin was purchased from the MCE company with the article number HY-10448; and artemisinin was purchased from the MCE company with the article number HY-B0094. In Embodiments 5 and 6, cannabidiol is purchased from Yuxi Hongbao Biotechnology Co., Ltd.; the active pharmaceutical ingredient of paroxetine hydrochloride is from Zhejiang Huahai Pharmaceutical Co., Ltd.; the active pharmaceutical ingredient of vitamin E (specifically in the form of a-tocopherol) is from Zhejiang NHU Co., Ltd.; anti-PD-1 is purchased from Bioxcell company (Ultra-LEAF™ Purified anti-mouse CD279 (PD-1, BE0146)); and corn oil is purchased from GOLD SUN Grain and Oil Co., Ltd.

The experimental cells used in the embodiments of the present invention were all purchased from the American Type Culture Collection (ATCC).

Embodiment 1 Effects of CBD on In Vitro Cultured Tumor Cells (1) Experimental Process 1. Effect of CBD on the Proliferation of In Vitro Cultured Tumor Cells Different types of tumor cells (RKO colorectal cancer cells, H1975 lung cancer cells, and A549 lung cancer cells) in the logarithmic growth phase were respectively inoculated into a 96-well plate at an inoculum density of $5 \times 10^3$ per well, and then, the tumor cells were placed into an incubator at 37° C. and 5% $CO_2$ for incubation for 24 h; a CBD mother solution (10 mM) was respectively diluted with culture medium to 5 µM, 10 µM, or 20 µM, and the culture medium in the 96-well plate was aspirated off, 100 µL of culture medium containing different concentrations of CBD was added to each well, a control well (0 µM CBD) was set, and the cells were continuously incubated for 24 h. After the culture was completed, the quantity of proliferating tumor cells was detected with an EdU kit (Beyotime, C0085S). Finally, a high-content imaging analysis system was used for photographing and the data were counted.

2. Effect of CBD on the Expression of PD-L1 in Tumor Cells

Different types of well-grown tumor cells (RKO colorectal cancer cells, H1975 lung cancer cells, and A549 lung cancer cells) with a density of 80% or more were respectively spread on a 6-well plate at a density of $5 \times 10^4$ cells/well, the volume of the suspension in each well was 2 mL, and the cells were subsequently placed in an incubator at 37° C. for culture. After 12 h of culture and when the cells had completely adhered to the wall, different concentrations (0 µM, 10 µM, 20 µM, 30 µM, and 40 µM) of CBD were added. After the cells were continuously cultured for 24 h, the culture was terminated, and subsequent detection was conducted.

After the culture was terminated, the cells were collected and washed with cold PBS 2 times. After the PBS residue was removed, a proper amount of cell lysate was added for cracking, and the cells were incubated on ice for 15 min and then centrifuged on a 4° C. centrifuge at 12,000 rpm for 15 min. The supernatant was carefully aspirated, the protein concentration was measured via the BCA method, a corresponding amount of loading buffer was added, the cells were evenly shaken and incubated in a 100° C. water bath for 10 min, and finally, the sample was subjected to a protein immunoblotting experiment.

3. Effect of CBD on the Expression of PD-L1 on the Membrane of Tumor Cells (1) Different types of tumor cells (RKO, HCT116 and HT29 colon cancer cells, and A549, H1975 and H460 lung cancer cells) in the logarithmic growth phase were respectively inoculated on a 6-well plate at an inoculum density of $2.5 \times 10^5$ cells/well with 2 mL/well and then placed in a cell incubator overnight incubation. The culture mixture was removed, CBD at different concentrations (0 µM, 5 µM, 10 µM, and 20 µM) was added for treatment for 24 h, the supernatant was removed, and the cells were washed with PBS 2 times, digested with pancreatin, centrifuged at 300×g and 4° C. for 5 min, and collected. The cells were washed with precooled PBS 2 times, centrifuged at 300×g and 4° C. for 5 min, and collected. The cells were washed 2 times with precooled PBS, 100 µL of PBS was added to resuspend the cells, an anti-PD-L1-Alexa Fluor 647 antibody was added, the cells were incubated at room temperature for 30 min and centrifuged at 300×g and 4° C. for 5 min, 300 µL of PBS was added to resuspend the cells in a flow tube, and an Alexa Fluor 647 signal was detected from the sample using a flow cytometer (excitation/emission wavelength of 647 nm/666 nm).

(2) The colorectal cancer cells (RKO) in the logarithmic growth phase were inoculated into a 6-well plate at a density of $2.5 \times 10^5$ cells/well, with a 2 mL volume of the suspension in each well. The plate was placed into a cell incubator for incubation overnight, the culture mixture was removed, 20 µM CBD was added for 12 h, the supernatant was removed, PBS was used for washing 2 times, paraformaldehyde was added for fixing for 15 min, 5% BSA was added for fixing for 1 h, PBST was used for washing 2 times, a PD-L1 antibody was added overnight incubation, a red fluorescent antibody was added for incubation at room temperature for 1 h, DAPI was added for staining for 10 min, and finally, a laser scanning confocal microscope was used for photographing and analysis.

4. Research of CBD on Enhancing In Vitro Killing of Tumor Cells by T Cells

RKO cells in the logarithmic growth phase were inoculated into a 12-well plate at a density of $5 \times 10^4$ cells/mL and placed in a 5% $CO_2$ incubator for growth adhering to a wall overnight. The supernatant was removed, CBD at different concentrations (0 µM, 5 µM, 10 µM, and 20 µM) was added, and the cells were coincubated for 12 h. NK-92 cells (T cells) were added at 1:500, the cells were cultured for 24 h, and a control group without the NK-92 cells was set at the same time. The supernatant was removed, PBS was used for washing 2 times, and 4% paraformaldehyde was added to fix the cells. Then, PBS was used for washing 2 times, crystal violet was added for dyeing for 30 min, and finally, redundant crystal violet was washed away with PBS, and photographing was performed to collect the data.

(II) Experimental Results

1. CBD has No Obvious Toxicity to Tumor Cells In Vitro

Figures 1, 2A, 2B, 2C:
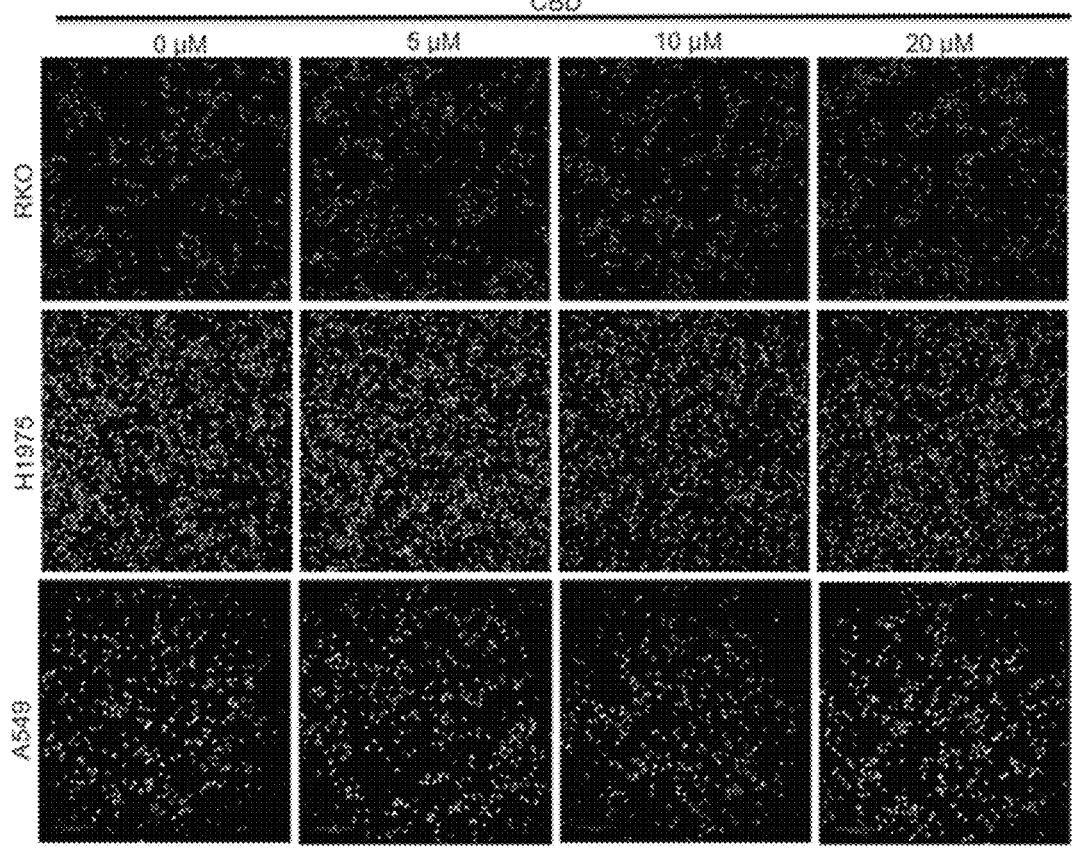
FIG. 1 is a comparison of the proliferation of different types of tumor cells treated with different concentrations of CBD.
FIGS. 2A-2C are a comparison of the expression of PD-L1 in different types of tumor cells treated with different concentrations of CBD.
Figures 3A, 3B, 3C, 3D, 3E, 3F:
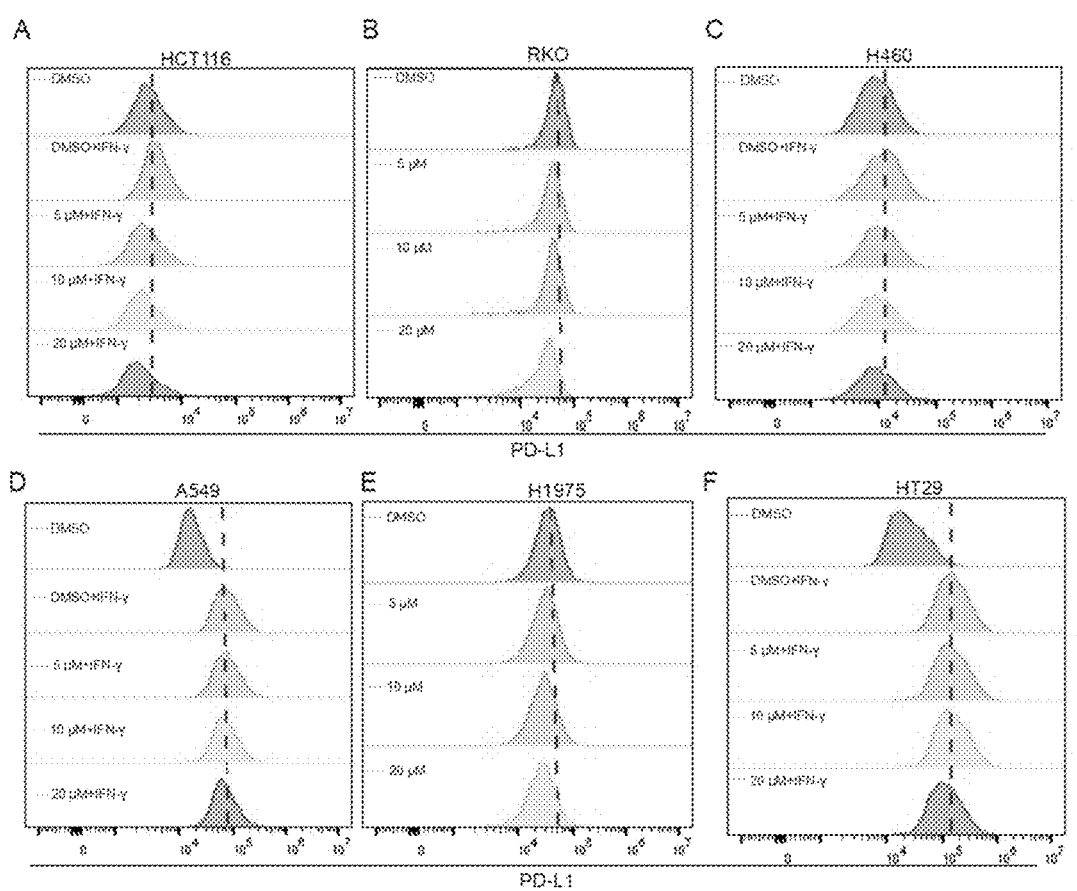

As shown in FIG. 1, the fluorescence intensity of the same type of tumor cells treated with different concentrations of CBD was not significantly different. This result indicated that when only CBD was added to tumor cells cultured in vitro, CBD was not significantly toxic to tumor cells. Further research on the anti-tumor mechanism of CBD is needed.

2. CBD Reduces the Expression of PD-L1 in Tumor Cells

As shown in A-C of FIG. 2, the Western blotting results revealed that CBD significantly inhibited the expression of PD-L1 in RKO colorectal cancer cells and H1975 and A549 lung cancer cells in a concentration-dependent manner at concentrations of 5 µM, 10 µM, and 20 µM.

3. CBD Reduces the Expression of PD-L1 on Cancer Cell Membranes in a Concentration- and Time-Dependent Manner.

As shown in FIGS. 3 and 4, the results of the flow assay revealed that CBD decreased the expression of PD-L1 on the cell membranes of RKO, HCT116 and HT29 colon cancer cells and A549, H1975 and H460 lung cancer cells in a concentration-dependent manner (5 µM, 10 µM, and 20 µM). The result of immunofluorescence showed that when at 20 µM, CBD time-dependently decreased the expression of PD-L1 on RKO colon cancer cell membranes.

4. CBD Enhances In Vitro Killing of Cancer Cells by T Cells

On the basis of the above experimental results 2 and 3, CBD and T cells (NK-92 cells) were added to tumor cells for in vitro coculture. The effect of CBD on the in vitro killing of tumor cells by T cells was studied.

As shown in FIG. 5, compared with the control, CBD+T cells coculture treatment significantly reduced the viability of RKO cells and induced their apoptosis. The results indicated that CBD enhanced the cytotoxicity of T cells to RKO cells by downregulating the expression of PD-L1 in RKO cells in a concentration-dependent manner at concentrations of 5 $\mu$M, 10 $\mu$M, and 20 $\mu$M.

Embodiment 2 In-Vivo Anti-Tumor Effects of Different Pharmaceutical Compositions of CBD and Paroxetine Hydrochloride (I) Experimental Process 1. MC38 colorectal cancer cells were inoculated into 6-week-old female C57BL/6 mice ($1\times10^6$ cells/mouse) to establish a subcutaneous tumor model. After the tumor volume reached 50 $mm^3$, the mice were grouped and administered according to the following pharmaceutical combinations: (1) control group (no administration), (2) anti-PD-1 (100 pg/time) group, (3) anti-CTLA4 (100 pg/time) group, (4) CBD (100 mg/kg) group, (5) CBD (100 mg/kg)+anti-CTLA4 (100 pg/time) group, (6) PAR (10 mg/kg) group, (7) PAR (10 mg/kg)+anti-CTLA4 (100 $\mu$g/kg) group, (8) CBD (100 mg/kg)+PAR (10 mg/kg) group, (9) vitamin E(a-to-copherol) (50 mg/kg)+thymosin (2 mg/kg) group, (10) CBD (100 mg/kg)+vitamin E($\alpha$-tocopherol) (50 mg/kg)+thymosin (2 mg/kg) group, (11) PAR (10 mg/kg)+vitamin E($\alpha$-tocopherol) (50 mg/kg)+thymosin (2 mg/kg), (12) PAR (10 mg/kg)+CBD (100 mg/kg)+vitamin E($\alpha$-tocopherol) (50 mg/kg)+thymosin (2 mg/kg) group, (13) CBD (100 mg/kg)+vitamin E($\alpha$-tocopherol) (50 mg/kg)+thymosin (2 mg/kg)+anti-CTLA4 (100 pg/time) group, (14) PAR (10 mg/kg)+vitamin E($\alpha$-tocopherol) (50 mg/kg)+thymosin (2 mg/kg)+anti-CTLA4 (100 g/time) group, and (15) CBD (100 mg/kg)+PAR (10 mg/kg)+vitamin E($\alpha$-tocopherol) (50 mg/kg)+thymosin (2 mg/kg)+anti-CTLA4 (100 pg/time) group. The tumor weight and volume, and body weight of the mice were monitored once every 2 days. The tumor volume was calculated as follows: tumor volume ($mm^3$)=0.5×(length)x(width)$^2$. The mice were sacrificed 14 days after drug administration, and the tumors were dissected.

The dissolving mode of the pharmaceutical composition was as follows: the pharmaceutical composition was dissolved in 10% DMSO+corn oil, the mice were gavaged with the pharmaceutical composition at 100 pl/mouse, and the mice in the control group were injected with the same volume of the solvent.

2. MC38 colorectal cancer cells were inoculated into 6-week-old female nude mice ($1\times10^6$ cells/mouse) to establish a subcutaneous tumor model. After the tumor volume reached 50 $mm^3$, the mice were grouped and administered according to the following pharmaceutical combinations: (1) control group, (2) CBD (100 mg/kg)+vitamin E($\alpha$-tocopherol) (50 mg/kg)+thymosin (2 mg/kg) group, (3) PAR (10 mg/kg)+vitamin E($\alpha$-tocopherol) (50 mg/kg)+thymosin (2 mg/kg) group, and (4) PAR (10 mg/kg)+CBD (100 mg/kg)+vitamin E($\alpha$-tocopherol) (50 mg/kg)+thymosin (2 mg/kg) group. The tumor weight and volume, and the body weight of the mice were monitored once every 2 days. The tumor volume was calculated as follows: tumor volume ($mm^3$)=0.5×(length)x(width)$^2$. The mice were sacrificed 14 days after drug administration, and the tumors were dissected.

(II) Experimental Results

1. Anti-Tumor Effects of Different Drug Combinations of CBD and Paroxetine Hydrochloride in Normal Mice As shown in A-D of FIG. 6 and Table 1, the results of the experiments in comparative groups (1), (2), (4) and (6) revealed that CBD and PAR had equivalent therapeutic effects and that CBD and PAR had equivalent therapeutic effects to those of an anti-PD-1 antibody commonly used in the prior art. The results of the experiments in comparative groups (1), (4), (6) and (8) revealed that compared with the single use of CBD and PAR, the combined use of CBD+PAR had a better tumor inhibition effect and synergistic effect.

After the T-cell enhancer (vitamin E($\alpha$-tocopherol)+thymosin) was added for treatment, the results of the experiments in the comparison groups (1), (4), (9) and (10) showed that the use of vitamin E($\alpha$-tocopherol)+thymosin had no obvious treatment effect. However, when CBD was combined with vitamin E($\alpha$-tocopherol)+thymosin, the treatment effect was better than that when CBD and vitamin E($\alpha$-tocopherol)+thymosin were used alone, and a synergistic effect existed.

Similarly, the results of the experiments in comparative groups (1), (6), (9) and (11) revealed that when PAR was combined with vitamin E($\alpha$-tocopherol)+thymosin, the treatment effect was better than that when PAR and vitamin E($\alpha$-tocopherol)+thymosin were used alone, and a synergistic effect also existed.

The results of the experiments in comparative groups (1), (8), (9) and (12) showed that, compared with the single use of CBD+PAR, and vitamin E($\alpha$-tocopherol)+thymosin, when CBD+PAR+vitamin E($\alpha$-tocopherol)+thymosin was combined, the tumor growth inhibition effect was stronger and a synergistic effect was detected.

The results showed that in the pharmaceutical composition provided by the present invention, when any one or two of CBD and PAR were combined with a T-cell enhancer (vitamin E($\alpha$-tocopherol)+thymosin), a synergistic effect was achieved, and a stronger anti-tumor effect was achieved.

Table 1

| | | | | | Comparison of Tumor Volume Growth in Each Group of Mice in Embodiment 2 | | | |
|---|---|---|---|---|---|---|---|---|
| | | | | | Group $mm^3$ | | | |
| Day | control | anti-PD-1 | anti-CTLA4 | CBD | CBD + anti-CTLA4 | PAR | PAR + anti-CTLA4 | CBD + PAR |
| 0 | 0 | 0 | 0 | 0 | 0 | 0 | 0 | 0 |
| 2 | 65.98 ± 22.43 | 64.65 ± 14.49 | 57.73 ± 16.08 | 54.99 ± 12.84 | 44.53 ± 14.07 | 43.63 ± 7.98 | 42.94 ± 13.38 | 49.72 ± 13.94 |

Table 1-continued

| 4 | 108.33 ± 55.94 | 92.70 ± 45.54 | 81.72 ± 23.73 | 70.96 ± 22.44 | 57.45 ± 7.94 | 68.09 ± 37.26 | 55.86 ± 13.83 | 59.94 ± 21.26 |
|---|---|---|---|---|---|---|---|---|
| 6 | 171.55 ± 84.69 | 106.33 ± 55.83 | 96.63 ± 48.65 | 87.63 ± 33.43 | 89.20 ± 39.07 | 83.54 ± 43.99 | 85.99 ± 34.87 | 68.64 ± 24.32 |
| 8 | 361.19 ± 240.97 | 185.21 ± 92.53 | 207.80 ± 144.33 | 178.79 ± 175.83 | 145.23 ± 77.16 | 177.63 ± 133.19 | 135.18 ± 77.23 | 91.37 ± 23.11 |
| 10 | 501.79 ± 254.17 | 338.24 ± 212.09 | 326.57 ± 245.38 | 279.84 ± 225.91 | 182.77± 106.13 | 263.45 ± 204.90 | 183.21 ± 112.75 | 132.23 ± 87.77 |
| 12 | 652.97 ± 382.81 | 388.92 ± 242.51 | 422.07 ± 299.81 | 399.70 ± 297.10 | 245.72 ± 183.45 | 393.48 ± 342.99 | 228.57 ± 147.22 | 192.45 ± 114.78 |
| 14 | 775.52 ± 441.20 | 493.44 ± 357.79 | 531.93 ± 271.20 | 493.09 ± 337.47 | 267.53 ± 220.33 | 510.89 ± 445.89 | 238.68 ± 181.66 | 239.76 ± 127.33 |
| 16 | 925.26 ± 454.61 | 570.04 ± 512.34 | 577.00 ± 311.69 | 600.09 ± 465 | 326.42 ± 197.05 | 608.61 ± 526.33 | 291.74 ± 180.14 | 333.17 ± 154.66 |

Comparison of Tumor Volume Growth in Each Group of Mice in Embodiment 2

| | Group mm$^3$ | | | | | | |
|---|---|---|---|---|---|---|---|
| Day | vitamin E + thymosin | CBD – vitamin E + thymosin | PAR + vitamin E + thymosin | CBD + PAR + vitamin E + thymosin | CBD + vitamin E + thymosin + anti-CTLA4 | PAR + vitamin E + thymosin – anti-CTLA4 | CBD + PAR+ vitamin E + thymosin + anti-CTLA4 |
| 0 | 0 | 0 | 0 | 0 | 0 | 0 | 0 |
| 2 | 47.02 ± 10.49 | 52.55 ± 20.78 | 46.14 ± 19.88 | 33.92 ± 8.86 | 34.59 ± 9.22 | 41.32 ± 20.36 | 29.35 ± 11.76 |
| 4 | 118.46 ± 45.21 | 72.39 ± 36.22 | 69.94 ± 32.80 | 47.24 ± 16.57 | 65.93 ± 29.11 | 59.81 ± 27.42 | 38.83 ± 13.02 |
| 6 | 133.53 ± 48.94 | 84.29 ± 34.21 | 79.07 ± 35.19 | 55.48 ± 23.93 | 74.50 ± 51.10 | 64.31 ± 28.75 | 42.67 ± 19.94 |
| 8 | 336.44 ± 192.71 | 142.92 ± 63.44 | 124.00 ± 56.04 | 90.60 ± 46.10 | 104.02 ± 59.03 | 90.94 ± 42.46 | 55.41 ± 32.24 |
| 10 | 501.18 ± 248.85 | 197.75 ± 121.38 | 182.78 ± 102.14 | 132.98 ± 65.88 | 165.63 ± 113.07 | 131.91 ± 86.70 | 69.75 ± 54.87 |
| 12 | 648.74 ± 358.80 | 271.35 ± 208.35 | 241.07 ± 213.23 | 175.95 ± 92.63 | 174.65± 120.74 | 138.05 ± 85.28 | 74.43 ± 61.86 |
| 14 | 755.28 ± 328.55 | 321.91 ± 305.13 | 272.21 ± 285.09 | 258.00 ± 141.74 | 189.56 ± 147.37 | 169.83 ± 158.35 | 115.31 ± 1 59.13 |
| 16 | 885.24 ± 320.8 | 376.62 ± 233.81 | 338.31 ± 232.80 | 301.45 ± 167.60 | 236.04 ± 142.57 | 248.16 ± 142.17 | 142.39 ± 1 67.54 |

2. 3 Compositions of CBD and Paroxetine Hydrochloride have No Anti-Tumor Effect in T Cells-Deficient Mice Based on the research results, 3 compositions with a better anti-tumor effect were injected into nude mice to explore the effect of the compositions on tumors in the immunodeficient mice.

The result was shown in A-D of FIG. 7, there was no significant difference in the size of the tumor volume among the 4 groups of mice; that is, 3 combined drugs (CBD+vitamin E(α-tocopherol)+thymosin; PAR+vitamin E(α-tocopherol)+thymosin; and PAR+CBD+vitamin E(α-tocopherol)+thymosin) had no therapeutic effect on the tumors of the nude mice.

The results indicated that the 3 compositions failed to exert a significant anti-tumor effect when no T cells were present in vivo.

3. 3 Compositions of CBD and Paroxetine Hydrochloride Combined with Other Immune Checkpoint Inhibitors have Better Antitumor Effects The present invention also attempted to add other immune checkpoint inhibitors to the 3 compositions with a better anti-tumor effect so as to obtain a pharmaceutical composition with a more excellent anti-tumor effect. An anti-CTLA4 antibody was used in the present embodiment.

As shown in A-D of FIG. 6, the results of the experiments in comparative groups (10) to (15) showed that the pharmaceutical composition exerted a synergistic effect and had a more significant anti-tumor effect after the anti-CTLA4 antibody was added to the 3 compositions, wherein the CBD+PAR+vitamin E(α-tocopherol)+thymosin+anti-CTLA4 composition exhibited the optimal anti-tumor effect compared with the other compositions.

Embodiment 3: The 3 Compositions Enhance the In Vitro Killing of Different Types of Tumor Cells by T Cells (I) Experimental Process Based on the research results of Embodiment 2, 3 compositions with a better anti-tumor effect were added to different types of tumor cells together with T cells. The specific experimental process was as follows:

RKO colorectal cancer cells, H1975 lung cancer cells, HepG2 liver cancer cells, MGC-803 gastric cancer cells, T24 bladder cancer cells, TE-5 esophageal cancer cells, MCF-7 breast cancer cells, and B16-F10 melanoma cells in the logarithmic growth phase were inoculated into a 12-well plate at a density of $5 \times 10^4$/mL, the cells were placed in an incubator at 37° C. and 5% $CO_2$ for growth adhering to a wall overnight, the supernatant was removed, the PAR+vitamin E(α-tocopherol)+thymosin composition, a CBD+vitamin E(α-tocopherol)+thymosin composition or a PAR+CBD+vitamin E(α-tocopherol)+thymosin composition culture medium were respectively added, a blank culture medium was used as a control group, the cells were coincubated for 12 h, the NK-92 cells were added at a ratio of 1:500, the cells were cultured for 24 h, the supernatant was removed, the PBS was used for washing 2 times, the 4% paraformaldehyde mixture was added to fix the cells, the PBS was used for washing 2 times, the crystal violet mixture was added for dyeing for 30 min, the excess crystal violet was washed away with PBS, and the photographing was performed to collect data.

(II) Experimental Results

As shown in A-D of FIG. 8 and E-H of FIG. 9, compared with the control group, the co-culture treatment of the 3 pharmaceutical compositions and the T cells significantly reduced the viability of RKO colorectal cancer cells, H1975 lung cancer cells, HepG2 liver cancer cells, MGC-803 gastric cancer cells, T24 bladder cancer cells, TE-5 esophageal cancer cells, MCF-7 breast cancer cells, and B16-F10 melanoma cells and induced the apoptosis of tumor cells. These results indicated that all 3 pharmaceutical compositions provided by the present invention can increase the cytotoxicity of T cells to tumor cells by down-regulating the expression of PD-L1 in tumor cells.

Embodiment 4 In-Vivo Anti-Tumor Effects of CBD and Artemisinin Composition, and CBD and Curcumin Composition (I) Experimental Process The present invention also involves the addition of other substances that may have a regulatory effect on the quantity or activity of T cells or have an anti-tumor effect to obtain different pharmaceutical compositions that exert synergistic effects. Artemisinin and curcumin+piperine were used in the present example. Among them, artemisinin has been reported to have anti-tumor effects, and curcumin and piperine have also been reported to have immunomodulatory effects.

The specific experimental process was as follows:

MC38 colon cancer cells were inoculated into 6-week-old female C57BL/6 mice ($1\times10^6$ cells/mouse) to establish a subcutaneous tumor model. After the tumor volume reached 50 mm$^3$, the mice in the artemisinin-administered groups were grouped and administered with the following pharmaceutical combinations: (1) control group, (2) CBD (100 mg/kg)+vitamin E($\alpha$-tocopherol) (50 mg/kg)+thymosin (2 mg/kg) group, and (3) CBD (100 mg/kg)+artemisinin (20 mg/kg)+vitamin E($\alpha$-tocopherol) (50 mg/kg)+thymosin (2 mg/kg). The mice in curcumin-administrated group were grouped and administered with the following pharmaceutical combinations: (1) control group, (2) CBD (100 mg/kg) group, (3) curcumin (50 mg/kg)+piperine (1 mg/kg) group, (4) CBD (100 mg/kg)+curcumin (50 mg/kg)+piperine group (1 mg/kg), and (5) CBD (100 mg/kg)+curcumin (50 mg/kg)+piperine (1 mg/kg)+vitamin E($\alpha$-tocopherol) (50 mg/kg)+thymosin (2 mg/kg).

The tumor growth volume of the mice was monitored once every 2 days. The tumor volume was calculated as follows: tumor volume (mm$^3$)=0.5×(length)x(width)$^2$. The mice were sacrificed 14 days after drug administration, and the tumors were dissected. The dissolving mode of the pharmaceutical composition was as follows: the pharmaceutical composition was dissolved in 10% DMSO+corn oil, the mice were gavaged with the pharmaceutical composition at 100 μl/mouse, and the mice in the control group were injected with the same volume of the solvent.

(II) Experimental Results

As shown in FIG. 10, compared with the control group, the tumor growth of the mice in the CBD+vitamin E($\alpha$-tocopherol)+thymosin group and the CBD+vitamin E($\alpha$-tocopherol)+thymosin+artemisinin group was inhibited, but there was no significant difference in the anti-tumor effects, indicating that the addition of the artemisinin did not further improve the anti-tumor effect of the CBD+vitamin E($\alpha$-tocopherol)+thymosin composition.

As shown in FIG. 11, compared with the control group, the tumor growth of the mice in the CBD group was inhibited to a certain degree, whereas the tumor growth of the mice in the curcumin+piperine group was not significantly inhibited. In addition, the pharmaceutical compositions of CBD+curcumin+piperine, CBD+curcumin+piperine+vitamin E($\alpha$-tocopherol), and CBD+curcumin+piperine+vitamin E($\alpha$-tocopherol)+thymosin had equivalent anti-tumor effects. Compared with CBD alone, the pharmaceutical compositions did not have obvious advantages, indicating that not all combinations can achieve synergistic anti-tumor effects.

To further verify the treatment effect of the pharmaceutical composition, when the T-cell enhancer was only vitamin E($\alpha$-tocopherol), the following experiment was conducted.

Embodiment 5 In-Vivo Anti-Tumor Effects of Different Pharmaceutical Compositions Combining CBD and Paroxetine Hydrochloride (1) Experimental Process MC38 colon cancer cells were inoculated into 6-week-old female C57BL/6 mice ($1\times10^6$ cells/mouse) to establish a subcutaneous tumor model. After the tumor volume reached 50 mm$^3$, the mice were grouped and administered with the following pharmaceutical combinations: (1) control group (no drug administration), (2) anti-PD-1 (100 pg per time) group, (3) vitamin E($\alpha$-tocopherol) (50 mg/kg) group, (4) CBD (100 mg/kg) group, (5) CBD (100 mg/kg)+vitamin E($\alpha$-tocopherol) (50 mg/kg) group, (6) PAR (5 mg/kg) group, (7) PAR (5 mg/kg)+vitamin E($\alpha$-tocopherol) (50 mg/kg) group, (8) CBD (100 mg/kg)+PAR (5 mg/kg) group, and (9) PAR (5 mg/kg)+CBD (100 mg/kg)+vitamin E($\alpha$-tocopherol) (50 mg/kg) group.

The tumor weight, tumor volume, and mouse body weight were monitored once every 2 days. The tumor volume was calculated as follows: tumor volume (mm$^3$)=0.5×(length)× (width)$^2$. The mice were sacrificed 14 days after drug administration, and the tumors were dissected.

The dissolving mode of the pharmaceutical composition was as follows: the pharmaceutical composition was dissolved in 10% DMSO+corn oil, the mice were gavaged with the pharmaceutical composition at 100 μl/mice, and the mice in the control group were injected with the same volume of the solvent.

(II) Experimental Results

1. Anti-Tumor Effects of Different Drug Combinations of CBD and Paroxetine Hydrochloride in Normal Mice As shown in A-D of FIG. 12 and Table 2, the results of the experiments in comparative groups (1), (2), (4), and (6) revealed that CBD and PAR had equivalent therapeutic effects and that CBD and PAR had equivalent therapeutic effects to those of an anti-PD-1 antibody commonly used in the prior art. The results of the experiments in comparative groups (4), (6), and (8) showed that compared with the single use of CBD and PAR, the combined use of CBD+PAR had a better tumor inhibition effect and synergistic effect.

When vitamin E($\alpha$-tocopherol) was added, a comparison of the experimental results of groups (1), (3), (4), and (5) revealed that vitamin E($\alpha$-tocopherol) alone had no significant therapeutic effect. However, when CBD was combined with vitamin E($\alpha$-tocopherol), the therapeutic effect was better than CBD or vitamin E($\alpha$-tocopherol) alone, showing a synergistic effect.

Similarly, comparing the experimental results of groups (1), (3), (6), and (7), when PAR was combined with vitamin E($\alpha$-tocopherol), the therapeutic effect was also better than PAR or vitamin E($\alpha$-tocopherol) alone, again demonstrating a synergistic effect.

Comparing the experimental results of groups (1), (3), (8), and (9), it was observed that the combination of CBD+PAR+vitamin E($\alpha$-tocopherol) had a stronger inhibitory effect on tumor growth compared to vitamin E($\alpha$-tocopherol) alone or CBD+PAR, indicating a synergistic effect.

These results indicate that in the pharmaceutical compositions provided by this invention, the combination of CBD and/or PAR with vitamin E($\alpha$-tocopherol) exerts a synergistic effect, producing a stronger anti-tumor effect.

(II) Experimental Results

As shown in A-D of FIG. 13 and A-D of FIG. 14, compared with the control group, CBD+vitamin E($\alpha$-tocopherol), PAR+vitamin E($\alpha$-tocopherol), CBD+PAR, and PAR+CBD+vitamin E($\alpha$-tocopherol) all enhanced the ability of T cells to kill RKO colorectal cancer cells, H1975 lung cancer cells, HepG2 liver cancer cells, MGC-803 gastric cancer cells, T24 bladder cancer cells, TE-5 esophageal cancer cells, MCF-7 breast cancer cells, and B16-F10 melanoma cells and induced the apoptosis of tumor cells. Furthermore, the PAR+CBD+vitamin E($\alpha$-tocopherol) combination exhibited stronger tumor-killing ability compared to CBD+vitamin E($\alpha$-tocopherol), PAR+vitamin E($\alpha$-tocopherol), and CBD+PAR alone. These results indicate that the

TABLE 2

Comparison of Tumor Volume Growth in Mice from Each Group in Embodiment 5

| | Group mm$^3$ | | | | | | | | |
|---|---|---|---|---|---|---|---|---|---|
| Day | control | PD-1 | VE | CBD | CBD + VE | PAR | PAR + VE | CBD + PAR | CBD + PAR + VE |
| 0 | 0 | 0 | 0 | 0 | 0 | 0 | 0 | 0 | 0 |
| 4 | 61.06 ± 24.82 | 54.69 ± 13.35 | 58.77 ± 13.71 | 63.99 ± 18.84 | 42.65 ± 8.348 | 44.74 ± 18.47 | 40.34 ± 17.99 | 50.10 ± 15.02 | 52.10 ± 12.95 |
| 6 | 166.54 ± 55.49 | 91.09 ± 21.88 | 124.89 ± 22.51 | 113.24 ± 27.18 | 90.20 ± 17.20 | 61.50 ± 24.22 | 65.91 ± 19.43 | 54.79 ± 20.25 | 54.20 ± 17.48 |
| 8 | 226.51 ± 55.18 | 104.39 ± 42.39 | 191.75 ± 59.69 | 120.48 ± 19.56 | 108.84 ± 39.41 | 85.83 ± 32.97 | 91.64 ± 17.96 | 68.63 ± 32.77 | 55.44 ± 23.03 |
| 10 | 420.06 ± 110.72 | 118.77 ± 21.50 | 284.59 ± 64.79 | 176.51 ± 42.50 | 163.69 ± 65.98 | 136.25 ± 49.31 | 120.16 ± 49.37 | 115.55 ± 53.97 | 78.20 ± 17.74 |
| 12 | 513.38 ± 161.01 | 163.17 ± 68.73 | 459.67 ± 130.48 | 241.75 ± 97.54 | 204.74 ± 92.50 | 176.62 ± 57.57 | 147.65 ± 15.84 | 135.08 ± 71.17 | 99.84 ± 22.86 |
| 14 | 638.49 ± 206.40 | 188.79 ± 75.52 | 532.81 ± 179.11 | 314.83 ± 103.70 | 264.94 ± 140.64 | 262.06 ± 41.51 | 217.65 ± 67.02 | 189.38 ± 79.76 | 131.40 ± 50.64 |
| 16 | 687.21 ± 177.98 | 211.82 ± 71.23 | 624.47 ± 203.01 | 359.72 ± 95.70 | 336.945 ± 136.10 | 302.90 ± 117.83 | 274.61 ± 69.01 | 225.75 ± 82.25 | 171.56 ± 53.86 |

Embodiment 6: PAR+CBD+Vitamin E($\alpha$-Tocopherol) Combination Enhances In-Vitro Killing of Different Types of Tumor Cells by T Cells (1) Experimental Process The combination of PAR+CBD+vitamin E($\alpha$-tocopherol), which exhibits good anti-tumor effects, was co-incubated with T-cells and different types of tumor cells for investigation. The specific experimental process was as follows:

RKO colorectal cancer cells, H1975 lung cancer cells, HepG2 liver cancer cells, MGC-803 gastric cancer cells, 124 bladder cancer cells, TE-5 esophageal cancer cells, MCF-7 breast cancer cells, and B 16-F10 melanoma cells in the logarithmic growth phase were inoculated into a 12-well plate at a density of 5×10$^4$ cells/mL. The cells were then placed in an incubator at 37° C. and 5% $CO_2$ for growth adhering to a wall overnight, and the supernatant was removed. CBD+vitamin E($\alpha$-tocopherol), PAR+vitamin E($\alpha$-tocopherol), CBD+-PAR, and PAR+CBD+vitamin E($\alpha$-tocopherol) were added to each well, a blank culture medium was set as a control group, and the cells were co-incubated for 12 h. Jurkat cells overexpressing PD-1 (T-cells) were added at 1:500, and the cells were cultured for 24 h. The supernatant was removed, PBS was used for washing 2 times, and 4% paraformaldehyde was added to fix the cells. PBS was then used for washing 2 times, crystal violet was added for 30 min, and finally, redundant crystal violet was washed away by PBS, and the photographing was performed to collect data.

CBD+vitamin E($\alpha$-tocopherol), PAR+vitamin E($\alpha$-tocopherol), CBD+PAR, and PAR+CBD+vitamin E($\alpha$-tocopherol) combinations provided by this invention can increase the cytotoxicity of T cells against tumor cells by downregulating the expression of PD-L1 in tumor cells (including colorectal cancer, lung cancer, liver cancer, gastric cancer, bladder cancer, esophageal cancer, breast cancer, and melanoma). Compared to other combinations, PAR+CBD+vitamin E($\alpha$-tocopherol) combination enhances the cytotoxicity of T cells against tumor cells and has a stronger synergistic effect.

In summary, the present invention provides an anti-tumor pharmaceutical composition based on immune checkpoint blockade, which comprises cannabidiol and/or paroxetine hydrochloride, as well as a T-cell enhancer. A series of in vitro and in vivo experiments have investigated the effects of pharmaceutical compositions on the expression of PD-L1 on the tumor cell membrane and its tumor-killing activity. The results showed that CBD and paroxetine hydrochloride can significantly down-regulate the expression of PD-L1 on the surface of cancer cells, thereby blocking the PD-1/PD-L1 signaling pathway and enhancing the ability of T cells to kill tumor cells. In addition, the present study demonstrated that the pharmaceutical ingredients provided by the present invention, namely, cannabidiol, paroxetine hydrochloride, and vitamin E($\alpha$-tocopherol)+thymosin, can exert a synergistic effect and improve the anti-tumor effect.

Although the content of the present invention has been described in detail through the aforementioned preferred embodiments, it should be recognized that the above description should not be considered as limiting the present invention. Upon reading the aforementioned content, it will be apparent to those skilled in the art that various modifications and alternations to the present invention can be made. Therefore, the claimed scope of the present invention should be defined by the appended claims.

The invention claimed is:

1. A method of treating a tumor in a human subject, the method comprising orally administering to the human subject paroxetine hydrochloride, α-tocopherol and thymosin, wherein the amounts of paroxetine hydrochloride, α-tocopherol and thymosin together are safe and effective to treat the tumor in the human subject.

2. The method of claim 1, further comprising orally administering cannabidiol to the human subject in an amount that, in combination with the amounts of paroxetine hydrochloride, α-tocopherol and thymosin, is safe and effective to treat the tumor in the human subject.

3. The method of claim 2, wherein the method comprises orally administering to the human subject an anti-tumor pharmaceutical composition consisting of the cannabidiol, the paroxetine hydrochloride, the α-tocopherol, the thymosin, and optionally one or more of a pharmaceutically acceptable carrier, an excipient, a wetting agent, an emulsifier, and a pH buffering agent.

4. The method of claim 2, wherein the ratio of amounts of cannabidiol to paroxetine hydrochloride to α-tocopherol to thymosin is 50:5:25:1.

5. The method of claim 1, wherein the paroxetine hydrochloride, the α-tocopherol and the thymosin are administered to the human subject in an anti-tumor pharmaceutical composition which further comprises at least one of a pharmaceutically acceptable carrier, an excipient, a wetting agent, an emulsifier, and a pH buffering agent.

6. The method of claim 5, wherein the anti-tumor pharmaceutical composition is in one of the following dosage forms: an oil, a granule, a tablet, a pulvis, a capsule, a microcapsule preparation, a pill, a powder, an oral liquid, a sol, a spray, and an atomizing agent.

7. A method of treating a tumor in a human subject, the method comprising orally administering to the human subject a safe and effective amount of paroxetine hydrochloride, cannabidiol, and α-tocopherol.

8. The method of claim 7, wherein the method comprises orally administering to the human subject an anti-tumor pharmaceutical composition comprising paroxetine hydrochloride, cannabidiol, and α-tocopherol.

9. The method of claim 8, wherein the anti-tumor pharmaceutical composition consists of the paroxetine hydrochloride, the cannabidiol, the α-tocopherol and optionally one or more of a pharmaceutically acceptable carrier, an excipient, a wetting agent, an emulsifier, and a pH buffering agent.

10. The method of claim 9, wherein the anti-tumor pharmaceutical composition is in one of the following dosage forms: an oil, a granule, a tablet, a pulvis, a capsule, a microcapsule preparation, a pill, a powder, an oral liquid, a sol, a spray, and an atomizing agent.

11. The method of claim 7, wherein the ratio of cannabidiol to paroxetine hydrochloride is 10:1.

12. The method of claim 7, wherein the ratio of cannabidiol to paroxetine hydrochloride is 20:1.

13. The method of claim 7, wherein the ratio of cannabidiol to paroxetine hydrochloride to α-tocopherol is 20:1:10.

\* \* \* \* \*